(12) United States Patent
Rule

(10) Patent No.: US 7,199,172 B2
(45) Date of Patent: Apr. 3, 2007

(54) METAL PHOSPHONATES AND RELATED NANOCOMPOSITES

(75) Inventor: Mark Rule, Atlanta, GA (US)

(73) Assignee: Plastic Technologies, Inc., Holland, OH (US)

( * ) Notice: Subject to any disclaimer, the term of this patent is extended or adjusted under 35 U.S.C. 154(b) by 0 days.

(21) Appl. No.: 11/110,269

(22) Filed: Apr. 20, 2005

(65) Prior Publication Data

US 2005/0239938 A1 Oct. 27, 2005

Related U.S. Application Data

(60) Provisional application No. 60/564,150, filed on Apr. 21, 2004.

(51) Int. Cl.
C08K 5/04 (2006.01)
(52) U.S. Cl. .................. 524/395; 524/133; 524/139
(58) Field of Classification Search ................ 524/133, 524/139, 395
See application file for complete search history.

(56) References Cited

U.S. PATENT DOCUMENTS

| | | | |
|---|---|---|---|
| 2,579,810 A | 12/1951 | Fields | |
| 3,014,949 A | 12/1961 | Birum et al. | |
| 4,224,203 A | 9/1980 | Minagawa et al. | |
| 4,232,146 A | 11/1980 | DiGiacomo et al. | |
| 4,256,872 A | 3/1981 | DiGiacomo et al. | |
| 4,260,542 A | 4/1981 | Joyce, III et al. | |
| 4,263,425 A | 4/1981 | Rothe et al. | |
| 4,267,308 A | 5/1981 | Parziale et al. | |
| 4,276,411 A | 6/1981 | DiGiacomo et al. | |
| 4,291,093 A | 9/1981 | Wishman et al. | |
| 4,291,111 A | 9/1981 | Lu | |
| 4,374,242 A | 2/1983 | Dines et al. | |
| 4,409,375 A | 10/1983 | Hartman et al. | |
| 4,421,887 A | 12/1983 | Horie et al. | |
| 4,436,899 A | 3/1984 | DiGiacomo et al. | |
| 4,446,061 A | 5/1984 | Joyce, III et al. | |
| 4,454,312 A | 6/1984 | Kuze et al. | |
| 4,501,615 A | 2/1985 | Reeder et al. | |
| 4,591,629 A | 5/1986 | El-Ghatta et al. | |
| 4,759,971 A | 7/1988 | Weissberger et al. | |
| 4,837,115 A | 6/1989 | Igarashi et al. | |
| 4,883,892 A | 11/1989 | Hardy et al. | |
| 4,962,228 A | 10/1990 | Hellring | |
| 4,972,011 A | 11/1990 | Richardson et al. | |
| 5,185,426 A | 2/1993 | Verheijen et al. | |
| 5,234,979 A | 8/1993 | Todtemann et al. | |
| 5,258,233 A | 11/1993 | Mills et al. | |
| 5,290,746 A | 3/1994 | Alberti et al. | |
| 5,310,771 A | 5/1994 | Walters | |
| 5,340,884 A | 8/1994 | Mills et al. | |
| 5,519,108 A | 5/1996 | Yuo et al. | |
| 5,573,820 A | 11/1996 | Harazoe et al. | |
| 5,608,032 A | 3/1997 | Yuo et al. | |
| 5,616,749 A | 4/1997 | Cheng et al. | |
| 5,650,469 A | 7/1997 | Long et al. | |
| 5,684,116 A | 11/1997 | Martl et al. | |
| 5,721,306 A | 2/1998 | Tsipursky et al. | |
| 5,760,121 A | 6/1998 | Beall et al. | |
| 5,830,992 A | 11/1998 | Whalen | |
| 5,844,032 A | 12/1998 | Serrano et al. | |
| 5,877,248 A | 3/1999 | Beall et al. | |
| 5,891,226 A | 4/1999 | Kleiner et al. | |
| 5,898,058 A | 4/1999 | Nichols et al. | |
| 5,902,539 A | 5/1999 | Schmidt et al. | |
| 5,998,528 A | 12/1999 | Tsipursky et al. | |
| 6,013,756 A | 1/2000 | Hagen et al. | |
| 6,042,908 A | 3/2000 | Long et al. | |
| 6,043,335 A | 3/2000 | Banach et al. | |
| 6,228,903 B1 | 5/2001 | Beall et al. | |
| 6,239,233 B1 | 5/2001 | Bell et al. | |
| 6,274,212 B1 | 8/2001 | Rule et al. | |
| 6,329,451 B2 | 12/2001 | Matsumoto et al. | |
| 6,365,071 B1 | 4/2002 | Jenewein et al. | |
| 6,365,659 B1 | 4/2002 | Aoyama et al. | |
| 6,365,661 B1 | 4/2002 | Fischer et al. | |
| 6,395,865 B2 | 5/2002 | Schmidt et al. | |
| 6,489,433 B2 | 12/2002 | Duan et al. | |
| 6,489,434 B2 | 12/2002 | Jen | |
| 6,506,853 B2 | 1/2003 | Duan | |

(Continued)

FOREIGN PATENT DOCUMENTS

DE 10132058 1/2003

(Continued)

OTHER PUBLICATIONS

Alberti, et al, Preparation of Nano-structured Polymeric Proton Conducting Membranes for Use in Fuel Cells.

(Continued)

Primary Examiner—Edward J. Cain
(74) Attorney, Agent, or Firm—Fraser Clemens Martin & Miller LLC; Donald R. Fraser

(57) ABSTRACT

Compositions comprising a polymer and an exfoliated metal phosphonate are provided. Processes for making such polymer compositions and articles formed from such polymer compositions are also provided. Compositions according to the invention are useful in polymer applications in which barrier properties are of concern, such as in plastic food and beverage containers.

53 Claims, No Drawings

U.S. PATENT DOCUMENTS

| | | |
|---|---|---|
| 6,541,598 B2 | 4/2003 | Duan et al. |
| 6,559,271 B2 | 5/2003 | Schaaf et al. |
| 6,586,558 B2 | 7/2003 | Schmidt et al. |
| 6,649,731 B2 | 11/2003 | Hori et al. |
| 6,680,094 B2 | 1/2004 | Kikuchi et al. |
| 6,703,474 B2 | 3/2004 | Fujimori et al. |
| 6,716,899 B1 | 4/2004 | Klatt et al. |
| 6,774,204 B1 | 8/2004 | Putzig |
| 2003/0109667 A1 | 6/2003 | Fujimori et al. |
| 2003/0144459 A1 | 7/2003 | Fujimori et al. |
| 2004/0024139 A1 | 2/2004 | Suzuki et al. |
| 2004/0044173 A1 | 3/2004 | Fujimori et al. |
| 2004/0059037 A1 | 3/2004 | Wang et al. |
| 2004/0249113 A1 | 12/2004 | Quillen et al. |
| 2005/0014929 A1 | 1/2005 | Rule |
| 2005/0075426 A1 | 4/2005 | Campbell et al. |
| 2005/0164092 A1* | 7/2005 | Alberti et al. .............. 429/306 |

FOREIGN PATENT DOCUMENTS

| | | | |
|---|---|---|---|
| EP | WO003081691 | * | 10/2003 |
| FR | 81 05797 | | 9/1982 |
| FR | 2502162 | | 9/1982 |
| JP | 48074550 | | 10/1973 |
| WO | WO 97/28218 A1 | | 8/1997 |
| WO | WO 03/081691 A2 | | 10/2003 |

OTHER PUBLICATIONS

Clearfield & Ortiz-Avila, Polyether and Polyimine Derivatives of Layered Zirconium Phosphates as Supramolecules.

Karlin, Kenneth D., Progress in Inorganic Chemistry, vol. 47, pp. 371-510.

* cited by examiner

METAL PHOSPHONATES AND RELATED NANOCOMPOSITES

CROSS-REFERENCE TO RELATED APPLICATION

This application claims priority to U.S. Provisional Application Ser. No. 60/564,150 filed on Apr. 21, 2004, the entire disclosure of which is incorporated herein by reference.

FIELD OF THE INVENTION

The invention relates to polymer compositions that comprise a polymer and an exfoliated metal phosphonate. The invention also relates to processes to produce such polymer compositions, and articles formed of the polymers of the invention.

BACKGROUND OF THE INVENTION

Polyesters, especially poly(ethylene terephthalate) (PET), are versatile polymers that enjoy wide applicability as fibers, films, and three-dimensional structures. A particularly important application for PET is for containers, especially for food and beverages. This application has seen enormous growth over the last 20 years, and continues to enjoy increasing popularity. Despite this growth, PET has some fundamental limitations that restrict its application in these markets. One such limitation is related to its permeability to gases such as oxygen and carbon dioxide. A second limitation is related to the tendency for pressurized PET containers to fail catastrophically when exposed to certain chemicals (a phenomenon known as stress-crack failure). A third limitation is related to the tendency for PET to have a high coefficient of friction when in contact with itself.

A number of technologies have been developed to overcome these limitations. For example, in order to improve the barrier properties of PET, polyester co-polymers and blends have been developed, such as PET containing 2,6-naphthtalenedicarboxylic acid and PET/MXD6 blends. Other developments include the use of organic and inorganic barrier coatings (such as epoxy-amines and $SiO_x$ coatings) and multilayer structures containing barrier polymers (such as EVOH and MXD6). To improve the stress-crack resistance of PET, higher molecular weight PET has been commercialized. To improve the sliding ability of PET in contact with itself, low aspect ratio inorganic additives such as silica, talc, and zeolites have been employed. However, each of these technologies has drawbacks. Thus, all of the aforementioned barrier technologies add substantially to the cost of PET packaging. Higher molecular weight PET is more difficult to process and is more expensive to produce. Additives such as silica, talc, and zeolites, while decreasing the sliding friction of PET, also increase the haze of the polymer.

A technology that could address each of these limitations of PET involves incorporation of high-aspect ratio nanomaterials into PET to form PET nanocomposites. Nanocomposites are polymeric materials that contain a particulate additive which has at least one dimension substantially less than a micron. When the additive also possesses a high aspect ratio (aspect ratio is defined as the ratio between the average of the lateral dimensions and the particle thickness; the lateral dimensions being the length and width of the particle), the resultant nanocomposites can exhibit improved barrier properties because the high aspect ratio of the additive increases the tortuosity of the path that gas molecules must travel in permeating the polymer. PET nanocomposites may also possess improved resistance to stress-crack failure because high-aspect ratio additives can provide a mechanism to hinder crack propagation. PET nanocomposites may also possess a reduced coefficient of friction through roughening of the PET surface, or by providing a surface with a higher hardness and/or lower coefficient of friction than PET itself.

In addition to polyesters, a number of other polymers are used in applications where permeation of gases, water, or organic molecules is detrimental. For example, polyolefins are widely used to make pipes for natural gas transport, for gas tanks in automobiles, and for food packaging applications. Polydienes are used widely as rubber for structures such as pneumatic tires. Polyvinyls such as polyvinyl chloride, polystryrene, and acrylonitrile-butadiene-styrene (ABS) are frequently used in applications where enhanced barrier performance would be desirable. Polyamides, which are used as barrier layers in some of these applications, would also benefit from the enhanced barrier performance arising from the incorporation of high aspect ratio materials. In all of these materials, use of high aspect ratio nanomaterials is limited or non-existent, because of the difficulties associated with incorporating exfoliated phyllosilicates into these polymers and maintaining the phyllosilicates in an exfoliated state.

Essentially all of the high-aspect ratio materials previously developed for use in polymers are based on phyllosilicates such as montmorillonite, a naturally occurring layered aluminosilicate clay that possesses charge-balancing monovalent and divalent ions, as well as traces of transition metal ions such as iron. Because of the high charge density on phyllosilicates, the individual layers are strongly attracted toward each other. To obtain high aspect-ratio nanomaterials, these layers must be separated, or exfoliated. In order to achieve exfoliation in nonaqueous environments, the metal ions are exchanged with hydrophobic quartemary ammonium salts to produce organically-modified phyllosilicates. These organically modified phyllosilicates can then be exfoliated in relatively polar polymers such as nylon 6, nylon 6/6, and MXD6. The lateral dimensions of the high-aspect ratio phyllosilicates are on the order of 250 nanometers.

In spite of the potential for phyllosilicates to be used to enhance the barrier properties of PET, little progress has been made in achieving PET/phyllosilicates polymer compositions. This lack of success is due to the chemical nature of PET; unlike nylons, there are a number of undesirable side reactions that can occur during the polymerization or processing of PET that are catalyzed by various metal ions and/or amine-containing compounds. For example, incorporation of relatively low levels of monovalent or divalent metal ions into PET can result in the rapid nucleation of the PET, rendering processing difficult or impossible. Transition elements such as iron can contribute to generation of acetaldehyde and color. Quaternary ammonium salts decompose at the temperatures required to melt-process PET, resulting in amines which rapidly cause formation of color and diethylene glycol in the PET, as well as loss of molecular weight. Finally, degradation of the quaternary ammonium salts can cause the exfoliated phyllosilicates to reaggregate, with a resultant loss of the high aspect ratios required to achieve the desired properties in PET compositions.

A further limitation of the phyllosilicates is that at an aspect ratio of 250, loadings of 2–10 weight percent in the polymer are necessary to achieve significant barrier improvement factors. Thus, in order to increase the barrier performance of MXD6 nylon by a factor of 4 requires 3.5 weight percent of an exfoliated phyllosilicates. The need for these high loadings, and the cost associated with modifying and incorporating the phyllosilicates into polymers places significant constraints on the price of the nanomaterials. In fact, it is for this reason that most of the nanocomposite research has focused on the modification and use of naturally occurring, abundant montmorillonite clays.

It therefore would be advantageous to develop layered nanomaterials which possess aspect ratios substantially greater than that available in the phyllosilicates, which are chemically benign to polymers such as polyesters, and which are comparatively easy to incorporate and exfoliate into polymers. It would be a further advantage if these nanomaterials could be readily synthesized from high-purity raw materials. It would be even a greater advantage if the chemical structure, functionality, and physical dimensions of the nanomaterials could be readily controlled. One class of materials which has some members that meet these criteria are layered metal phosphonates. Layered metal phosphonates are a subset of all metal phosphonates. Depending on the reactants, stoichiometries, and synthesis conditions, metal phosphonates can also form one-dimensional chains, one-dimensional nanotubes, three-dimensional microporous frameworks, and non-porous three-dimensional frameworks.

Although layered metal phosphonates have been known for a number of years, there have been few attempts to incorporate them into polymers. Thus U.S. Pat. No. 4,232,146 discloses the preparation of layered tetravalent metal phosphonates, but does not disclose exfoliation of the metal phosphonates in a polymer matrix. French patent application 81 05797 discloses polyester compositions with improved crystallization rates that comprise a) a thermoplastic polyester, b) a nucleating agent chosen from metal salts of organophosphonic, organophosphinic, and organophosphonous acids, and c) a plasticizing agent. However, there is no teaching of the use of layered metal phosphonates or exfoliation of the metal phosphonate in the polyester. U.S. Pat. No. 4,759,971 discloses the use of layered tetravalent metal phosphonates as adhesion promoters in polymer matrices but does not disclose exfoliation of the tetravalent metal phosphonate. JP 48074550 describes the use of metal salts of arylphosphonates as nucleating agents for polyesters. Once again, there is no teaching of the use of layered metal phosphonates or exfoliation of the metal phosphonates.

A need remains, therefore, for improved polymer compositions that include metal phosphonates and for related processes and articles.

SUMMARY OF EXEMPLARY EMBODIMENTS OF THE INVENTION

The invention provides polymer compositions that comprise a polymer and an exfoliated layered metal phosphonate. The invention also relates to processes to produce such polymer compositions, and articles formed of the polymers of the invention.

Processes for making polymer compositions according to the invention include a step of incorporating an effective amount of a layered metal phosphonate. The metal phosphonate is capable of exfoliating and/or remaining exfoliated during melt processing of the polymer. The step of incorporating the exfoliated layered metal phosphonate can comprise any suitable process, including mixing an unexfoliated layered metal phosphonate with molten polymer, mixing an exfoliated or unexfoliated layered metal phosphonate with polymer precursors followed by polymerization, mixing an exfoliated dispersion of a layered metal phosphonate with a polymer solution, and mixing metal phosphonate precursors with a polymer solution, polymer melt, or polymer dispersion.

Polymer compositions according to the invention comprise a polymer and an exfoliated layered metal phosphonate. Any suitable polymer and any suitable metal phosphonate can be used in the compositions of the invention. Exemplary embodiments of polymer compositions according to the invention comprise poly(ethylene terephthalate) and a suitable metal phosphonate.

Articles according to the invention comprise a polymer composition that includes an exfoliated layered metal phosphonate. The articles of the invention can have any suitable shape, configuration, and form. Exemplary embodiments of articles according to the invention include containers for holding compositions for ingestion by an animal, such as containers for holding food or beverages for human consumption. An article according to one exemplary embodiment of the invention comprises a beverage container formed of a polymer composition that includes poly(ethylene terephthalate) and an exfoliated layered metal phosphonate. Other exemplary embodiments of articles include containers and vessels for containing hydrocarbons such as natural gas, gasoline, or oil products. Further embodiments include flexible articles that exhibit reduced loss or ingress of permanent gases such as oxygen, nitrogen, helium, and the like.

DETAILED DESCRIPTION OF EXEMPLARY EMBODIMENTS OF THE INVENTION

The following detailed description describes various exemplary embodiments of the invention. The description serves to enable one skilled in the art to make and use the invention, and is not intended to limit the scope of the invention or its protection in any manner.

The invention provides processes for making polymer compositions that include an exfoliated layered metal phosphonate. In the processes of the invention, a metal phosphonate is incorporated into a polymer. Any suitable layered metal phosphonate can be used in the processes of the invention. The layered metal phosphonate need only have the desired ability to exfoliate in the polymer matrix and/or remain exfoliated in the polymer matrix, and have sufficient lateral dimensions to afford suitable enhancement of the properties of the polymer.

A range of soluble metal salts spontaneously form water-insoluble layered metal phosphonates on admixture of aqueous solution of soluble metal salts with phosphonic acid derivatives. In recent years, a number of such metal phosphonates have been prepared and characterized. Much of the work with metal phosphonates has been directed toward preparing layered zirconium phosphonates, with the intent to produce new materials suitable as adsorbents and catalysts. A review of these materials can be found in *Progress in Inorganic Chemistry*, Volume 47 pages 371–510 (ISBN 0-471-24039-7). An appeal of the this chemistry is that by varying the nature of the R-group on the phosphonic acid, the spacing between the layers and the porosity of the resultant metal phosphonates can be readily varied. A drawback of the tetravalent metal phosphonates such as zirconium phosphonates derivatives is that they generally exhibit very poor crystallinity and possess low aspect ratios, because the lateral dimensions of the crystals formed tend to be only a few tens of nanometers. Even when heroic efforts are taken to increase the crystallinity of tetravalent metal phosphonates by extended ageing at elevated temperatures in highly acidic media, the lateral dimensions achieved seldom exceed 200 nanometers. In contrast, by varying the conditions of precipitation and crystal growth, the particle size of divalent metal phosphonates can be varied from submicron particles to crystals with lateral dimensions in the range of 1–100 microns. However, all metal phosphonates are generally regarded as being extremely difficult to exfoliate. While metal phosphonates are electrically neutral and thus do not possess the strong electrostatic charges found in the montmorillonite clays, the Van der Waals forces between the layers are generally regarded as being more than sufficient to prevent exfoliation, even on shearing or ultrasonication. This is particularly regarded to be true for particles with large lateral dimensions.

The inventor has surprisingly discovered that even large crystals of some metal phosphonates can be readily exfoliated in a polymer matrix, if the metal phosphonates are prepared by reacting a soluble metal salt with a properly selected phosphonic acid or mixtures of properly selected phosphonic acids such that either the resulting metal phosphonate possesses a reduced level of Van der Waals force between the layers and/or an increased affinity for the polymer matrix. Metal phosphonates prepared by reacting a soluble metal salt with a long-chain alkyl phosphonic acid or a mixture of phosphonic acids are advantageous in the invention. Also, the inventor has discovered that metal phosphonates prepared by reacting a metal salt with a mixture of phosphonic acids having R groups of differing lengths are particularly advantageous in the invention. It is believed that metal phosphonates prepared in this manner can have a random arrangement of R-groups. In such a random arrangement, the longer R-groups determine the spacing between the layers while the presence of the shorter R-groups impedes the development of strong Van der Waals forces that would hold the layers together and prevent exfoliation. The presence of the shorter R-groups also facilitates the intercalation of low molecular weight compounds between the layers, which can aid in the exfoliation of these layered metal phosphonates. In general, the greater the interlayer spacing the greater the ease of exfoliation; also, in general as the amount of the shorter R-group approaches 50 mole % the greater the ease of exfoliation. The shorter R-group does not need to be substantially shorter than the longer R-group in order to impede the development of strong Van der Waals forces between the metal phosphonate layers.

Non-limiting examples of moieties that can advantageously be used as the R-groups in the metal phosphonates include hydrogen, hydroxyl, alkyl, alkoxy, aryl, aryloxy, and moieties incorporating more than one such functionality. For example, suitable R-groups include hydrogen (with the starting phosphonic acid being phosphorous acid); hydroxyl (with the starting phosphonic acid being phosphoric acid); methyl, ethyl, propyl, butyl, hexyl, octyl, decyl, dodecyl, or higher alkyl phosphonic acids; phenyl, benzyl, biphenyl, and substituted aryl phosphonic acids; oxyethyl, oxypropyl, oxybutyl, oxyoctyl, poly(ethyleneoxy)phenyl and substituted poly(ethyleneoxy)phenyl phosphonic acids (also known generically as phosphoric acid monoesters). The R-groups can also contain additional functional groups, such as carboxyl, hydroxyl, amino, and halo groups. The R-groups advantageously possess chemical and thermal stability at the melt processing temperatures required for polymers. The inventor has determined that hydrogen, hydroxyl, alkyl, and phenyl are particularly advantageous R-groups because metal phosphonates containing these R-groups exhibit high thermal and thermo-oxidative stability. Further, mixtures of these R-groups can provide the desired variation in length for the R-groups.

Metal ions suitable for preparation of layered metal phosphonates include but are not limited to titanium, zirconium, hafnium, tin, vanadium, lanthanum, aluminum, cerium, molybdenum, uranium, thorium, magnesium, calcium, strontium, barium, manganese, nickel, cobalt, iron, copper, cadmium, and zinc. Of these, divalent metal ions are considered advantageous because they tend to form crystals with larger lateral dimensions that upon exfoliation yield individual layers with higher aspect ratios than those from metal phosphonates formed from trivalent and tetravalent metal ions. Of the divalent metal ions, magnesium, calcium, and zinc are particularly advantageous due at least in part to their low toxicity, low cost, and ease of reaction to form a range of layered metal phosphonates. Since the basal area of layered metal phosphonates is essentially invariant regardless of the metal ion selected, it is contemplated that a metal phosphonate of the present invention may comprise more than one metal ion. It is also contemplated that more than one exfoliated layered metal phosphonate can be incorporated into a polymer, since different metal phosphonates with different compositions and/or different lateral dimensions are anticipated to provide different levels of barrier improvement, stress-crack improvement, and coefficient of friction improvement.

Any polymer can be used for which it is desired to provide polymer compositions that may have the properties described herein, although the existence and/or degree of these characteristics are not a required element of any aspect of the invention. Non-limiting examples of suitable polymers for use in the invention include polyesters, polyolefins, polydienes, polyvinyls, polyamides, polysulfides, polyketones, polyethers, and polycarbonates. Examples of non-polyester polymers contemplated by this invention include but are not limited to polyethylene, polypropylene, polybutene, polybutadiene, poly(butadiene-styrene), polyisoprene, poly(vinyl chloride), polystyrene, polyacrylonitrile, poly(methyl methacrylate), poly(vinyl alcohol), poly(ethylene-vinyl alcohol), poly(caprolactam), poly(hexamethyleneadipamide), poly(m-xylylenediamineadipamide), poly(phenylene sulfide), poly(ether-ether ketone), poly (ethyleneketone), polyacetal, and poly(bis-phenol A carbonate). Homopolymers, copolymers, and blends of these polymers are also contemplated. In exemplary embodiments of the invention, a polyester is used. Examples of polyesters contemplated by this invention include but are not limited to poly(ethylene terephthalate), poly(ethylene naphthalate), poly(cyclohexylenedimethylene terephthalate), poly(ethylene isophthalate), poly(butylene terephthalate), and copolymers and blends of these polyesters.

The layered metal phosphonate can be added to the polymer at any point during a process for making the polymer composition. For example, the metal phosphonate can be added to molten polymer or to polymer precursors. Also, metal phosphonate precursors can be added to a polymer solution, a polymer melt, or a polymer dispersion. It is advantageous to maximize the degree of exfoliation of the metal phosphonates within the polymer matrix. Therefore, the metal phosphonates are advantageously added at a point in a process at which sufficient melt mixing and exfoliation can occur before forming the final article. For some applications and/or metal phosphonate compositions, it is sufficient to add the metal phosphonates as powders or as dispersions immediately prior to the injection or extrusion molding process. However, it is possible to add the metal phosphonate before or during the polymerization process. It is also possible to prepare a dispersion of the metal phosphonate in the polymer as a concentrate, and then melt-mix the resultant concentrate with the bulk polymer prior to formation of the final article. Other methods for incorporation of exfoliated metal phosphonates into polymers include adding the metal phosphonate to solutions or dispersions of the polymer, followed by removal of the solvent or dispersant.

The layered metal phosphonates can be exfoliated in the polymers as a polymers, and no additional additives (such as quaternary ammonium salts) are required to enhance the ability of the metal phosphonates to exfoliate. Alternatively, the layered metal phosphonates can be exfoliated in a solvent such as ethylene glycol, dimethoxyethane, dimethyl formamide, xylene, hexane, or mineral oil. The rate and degree of exfoliation may be increased by the application of heat, ultrasound, mixing, or milling.

The amount of metal phosphonate added to the polymer depends on the degree of property enhancement desired and the aspect ratio of the exfoliated metal phosphonate. For example, if a barrier enhancement factor of 2 were desired in a polyester such as amorphous PET and the metal phosphonate has an aspect ratio of 5,000, then 400 ppm by volume of the metal phosphonate may be required. If a barrier enhancement factor of 4 is desired, then either 1,200 ppm by volume of a metal phosphonate with an aspect ratio of 5,000, or 400 ppm by volume of a metal phosphonate with an aspect ratio of 15,000 may be utilized. For a metal phosphonate where the thickness of the individual layers is 1.5 nanometers and the aspect ratio is 15,000, the lateral dimension of the particles would be about 22 microns.

The inventor has discovered that metal phosphonates with lateral dimensions greater than about 0.25 microns are advantageous at least because they enable suitable barrier enhancement with acceptable loadings of exfoliated metal phosphonate. While metal phosphonates with lateral dimensions less than about 0.25 microns will also provide barrier enhancement, the loadings required to achieve significant barrier enhancements are substantially greater than those required for particles with larger lateral dimensions. Metal phosphonates with lateral dimensions greater than about 1 micron are considered particularly advantageous for this reason, as are metal phosphonates with lateral dimensions greater than about 5 microns. The inventor notes that metal phosphonates with lateral dimensions greater than about 10 microns provide particular advantage with respect to barrier enhancement balanced against acceptable loadings. Contrary to the teachings in the literature, many layered metal phosphonates are robust and substantially retain their lateral dimensions even after aggressive blending into polymer compositions.

The invention also provides articles formed of the polymer compositions of the invention. The articles of the invention can have any suitable shape, configuration, and form. Exemplary embodiments of articles according to the invention include containers for holding compositions for ingestion by an animal, such as containers for holding beverages for human consumption. An article according to one exemplary embodiment of the invention comprises a beverage container formed of a polymer composition that includes poly(ethylene terephthalate) and an exfoliated metal phosphonate. Other articles contemplated in this invention include but are not limited to pipes, tubes, tanks, fibers, films, and membranes. It is anticipated that these articles can comprise monolayer constructions, wherein the exfoliated layered metal phosphonate is dispersed throughout the polymer matrix. It is also anticipated that these articles can comprise multilayer constructions, wherein the exfoliated layered metal phosphonate is substantially located in one or more layers of the multilayer construction.

Articles according to the invention can be formed using the polymer compositions according to the invention and any suitable forming technique. Injection molding is one exemplary technique for forming articles according to the invention.

EXAMPLES

The following Examples describe specific exemplary embodiments of the invention, and are provided to more fully describe the invention. They are not, however, intended to represent any limitation as to the scope of the invention or its protection.

Example 1

Preparation of zinc(phosphite-co-phenylphosphonate), $Zn(O_3PH)_{0.5}(O_3PPh)_{0.5}$: 10.9 grams of zinc acetate dihydrate (0.05 moles) was dissolved in 50 ml of hot water. Separately, 3.95 grams (0.025 moles) of phenylphosphonic acid and 2 grams of phosphorous acid (0.025 moles) were dissolved in hot water. The two portions were slowly combined with stirring. There was an immediate precipitation of zinc(phenylphosphonate-co-phosphite). After stirring for 2 hours, the precipitate was isolated by filtration. After drying, there was obtained 8.5 grams (92% yield) of zinc(phenylphosphonate-co-phosphite). Microscopic examination of the material showed it to consist of agglomerates of crystals, with an average particle size of the agglomerates in the range of 20–50 microns. A small portion of the agglomerated crystals were mixed in mineral oil with a spatula. Examination of this milled material showed that the individual crystals had lateral dimensions in the range of 5–10 microns.

Example 2

Preparation of zinc (phosphite-co-octylphosphonate) $Zn(O_3PH)_{0.4}(O_3PC_8H_{17})_{0.6}$: 11.6 grams of octylphosphonic acid (0.06 moles) and 3.3 grams (0.04 moles) of phosphorous acid were dissolved in water. This solution was heated to ~50–70 deg C., then 21.9 grams of zinc acetate dihydrate (0.10 moles) dissolved in hot water was added dropwise with stirring. After addition was complete, mixture was heated for an additional hour, then was allowed to cool to room temperature overnight. Product was gravity filtered and air dried. Yield was 80%. Microscopic examination of the crystals showed them to have lateral dimensions on the order of 20–30 microns.

Example 3

Preparation of zinc (phosphite-co-phenylphosphonate), $Zn(O_3PH)_{0.5}(O_3PPh)_{0.5}$: 43.8 grams of zinc acetate tetrahydrate (0.20 moles) was dissolved in 300 ml of hot water. Separately, 15.8 grams of phenylphosphonic acid (0.10 moles) and 8.2 grams of phosphorous acid (0.10 moles) were dissolved in 500 ml of hot water. The zinc solution was added dropwise to the phosphonic acid with stirring. After addition was complete, the resulting slurry was held at 75 deg C. for an additional 2 hours. The product was then gravity filtered and the filter cake rinsed with hot water. After drying, there was obtained 34.0 grams (93% yield) of crystalline material. Microscopic examination of the crystals showed them to have an individual particle size in the range of 30–40 microns.

Example 4

Preparation of zinc(phosphite-co-benzylphosphonate), $Zn(O_3PH)_{0.5}(O_3PCH_2Ph)_{0.5}$: 24.1 grams of zinc acetate dihydrate (0.11 moles) was dissolved in 250 ml of hot water. Separately, 8.7 grams (0.051 moles) of benzylphosphonic acid and 4.2 grams of phosphorous acid (0.051 moles) were dissolved in 250 ml hot water. The zinc solution was added dropwise to the phosphonic acid solution with stirring. The resulting slurry was held at 75 deg C. for an additional 2 hours. The product was then gravity filtered and the filter cake rinsed with hot water. After drying, there was obtained 17.1 grams (88% yield) of crystalline material. Microscopic examination of the crystals showed them to have an individual particle size in the range of 20–30 microns.

Example 5

Preparation of zinc (phosphite-co-octylphosphonate) $Zn(O_3PH)_{0.4}(O_3PC_8H_{17})_{0.6}$: 23.3 grams of octylphosphonic acid (0.12 moles) and 6.6 grams (0.08 moles) of phosphorous acid were dissolved in water. This solution was heated to ~50–70 deg C., then 43.8 grams of zinc acetate dihydrate (0.20 moles) dissolved in hot water was added dropwise with stirring. After addition was complete, mixture was heated for an additional hour, then was allowed to cool to room temperature overnight. Product was gravity filtered and air dried. Yield was 84%. Microscopic examination of the crystals showed them to have an individual particle size of 30–40 microns wide and up to 200 microns in length.

Example 6

Preparation of Zinc(phosphite-co-decylphosphonate), $Zn(O_3PH)_{04}(O_3PC_{10}H_{21})_{0.6}$. 26.6 grams of decylphosphonic acid (0.12 moles) and 6.6 grams of phosphorous acid (0.08 moles) were dissolved in water. This solution was heated to ~50–70 deg C., then 43.8 grams of zinc acetate dihydrate (0.20 moles) was dissolved in water and added dropwise with stirring. After addition was complete, mixture was heated for an additional hour, then was allowed to cool to room temperature for 4 hours. After filtration, the precipitate was dried on a steam bath. Microscopic inspection showed the individual crystals were elongated tablets (20–30 microns×200 microns).

Example 7

Preparation of calcium bis(phenylphosphonate), $Ca(HO_3PPh)_2$: 5.9 grams of calcium nitrate tetrahydrate (0.025 moles) was dissolved in 20 ml of hot water. Separately, 7.9 grams of phenylphosphonic acid (0.05 moles) was dissolved in 20 ml of hot water. The two portions were combined with stirring. The resulting solution was then held at 80 deg C. Over the course of six hours, large crystals of calcium bis(phenyl phosphonate) precipitated. After cooling to room temperature, the water slurry was filtered and the filter cake rinsed with hot water. After drying, there was obtained 6.5 grams (73% yield) of crystalline material. Microscopic examination of the crystals showed them to have an individual particle size of in the range of 100–250 microns.

Example 8

Preparation of calcium(phosphate-co-phenylphosphonate), $Ca(O_3POH)_{0.5}(O_3PPh)_{0.5}$. Prepared by the dropwise addition of 1.0 moles of calcium acetate monohydrate dissolved in 500 ml of hot water to a solution of 0.5 moles of phosphoric acid and 0.5 moles of phenylphosphonic acid dissolved in 500 ml of hot water. After addition was complete, the product was gravity filtered and air dried. Individual particle size was 50–100 microns. Yield was 147 grams, 89% of theory.

Example 9

Calcium(phosphite-co-phenylphosphonate), $Ca(O_3PH)_{0.4}(O_3PPh)_{0.6}$. Prepared by the dropwise addition of 0.135 moles of calcium acetate in water (20 grams) to a solution of 0.04 moles of phosphorous acid (3.3 grams) and 0.06 moles of phenylphosphonic acid (9.5 grams). Particle size was 50–100 microns.

Example 10

Calcium(phosphate-co-benzylphosphonate), $Ca(O_3POH)_{0.4}(O_3PCH_2Ph)_{0.6}$. Prepared by the dropwise addition of 0.05 moles of calcium acetate in water to a solution of 0.02 moles of phosphoric acid and 0.03 moles of benzylphosphonic acid. Precipitation occurred over several minutes.

Example 11

Calcium(phosphite-co-octylphosphonate), $Ca(O_3PH)_{0.4}(O_3PC_8H_{17})_{0.6}$. 7.8 grams of octylphosphonic acid (0.03 moles) and 1.6 grams of phosphorous acid (0.02 moles) were dissolved in water. This solution was heated to ~50–70 deg C., then 21.9 grams of calcium acetate monohydrate (0.05 moles) was dissolved in water and added dropwise with stirring. After addition was complete, mixture was heated for an additional hour, then was allowed to cool to room temperature for 4 hours. Product was then filtered and air dried.

Example 12

Magnesium(phosphite-co-phenylphosphonate), $Mg(O_3PH)_{0.5}(O_3PPh)_{0.5}$. Prepared by the dropwise addition of 0.10 moles of magnesium acetate in water to a solution of 0.05 moles of phosphorous acid and 0.05 moles of phenylphosphonic acid, followed by heating to reflux for 2 hours. Precipitation occurred over several hours. Particle size was 50–100 microns.

Example 13

Magnesium(phosphite-co-decylphosphonate), $Mg(O_3PH)_{0.5}(O_3PC_{10}H_{21})_{0.5}$. 11.1 grams of decylphosphonic acid (0.05 moles) and 4.1 grams of phosphorous acid (0.05 moles) were dissolved in hot water, and 21.4 grams of magnesium acetate tetrahydrate (0.10 moles) dissolved in hot water was added dropwise with stirring. After the addition was complete (~40 minutes), the product was allowed to stand at ~75 deg C. for another hour. The product was then allowed to cool to room temperature and was gravity filtered. The precipitate was washed twice with hot water and the product dried on a steam bath. Yield of product was 10.5 grams (60% yield). Optical microscopy found plate-like particles with lateral dimensions on the order of 30–70 microns.

Example 14

Zinc octylphosphonate, $Zn(O_3PC_8H_{17})$. 21.9 grams (0.1 moles) of zinc acetate tetrahydrate in 250 ml water was added dropwise with stirring to 19.4 grams (0.1 moles) of octylphosphonic acid dissolved in 500 ml water. The temperature and gravity filtered. Optical microscopy found elongated particles with lateral dimensions on the order of 15–30 microns.

Example 15

Calcium bis(octylphosphonate), $Ca(HO_3PC_8H_{17})_2$. 8.8 grams (0.05 moles) of calcium acetate hydrate was dissolved in water and was added dropwise with stirring to 19.4 grams of octylphosphonic acid (0.10 moles) dissolved in 500 ml water containing a few mls of hydrobromic acid. The resultant product was then held at 75 deg C. for four hours, then cooled to room temperature and gravity filtered. Yield was ~21 grams of very large flat rhomboid-shaped crystals (40–100 micron particle size). The large particle size was due to crystal growth promoted by the presence of the hydrobromic acid.

Example 16

Zinc(phosphite-co-phenylphosphonate) from Example 1 was melt blended into 0.84 dl/g IV PET at a 500 ppm loading via a single screw extruder. The resulting amorphous polymer was identical in appearance with respect to color and haze when compared to a PET control processed under the same conditions

Example 17

PET pellets containing 500 ppm of zinc(phosphite-co-phenylphosphonate) from Example 16 were subjected to a second extrusion through a single screw extruder The resulting polymer was then solid-state polymerization to rebuild the IV to 0.82 dl/g. It was observed that the PET containing zinc(phosphite-co-phenylphosphonate) exhibited about a 17% slower rate of IV increase to that observed for at PET control under identical conditions. Modeling of the solid-state polymerization reaction showed that this decrease in rate of IV build was consistent with a barrier improvement factor (BIF) of about 1.5.

Example 18

PET from Examples 16 and 17 was injection molded into preforms and blown into bottles. The bottles were then tested for IV, color, haze, stress-crack failure coefficient of friction (COF), and oxygen barrier testing. The results of that testing is presented in Table 1.

TABLE 1

| Analysis | PET | PET + mineral oil | Example 16 PET + 500 ppm $Zn(O_3PH)_{0.5}(O_3PPh)_{0.5}$ | Example 17 PET + 500 ppm $Zn(O_3PH)_{0.5}(O_3PPh)_{0.5}$ |
|---|---|---|---|---|
| IV | 0.767 | 0.771 | 0.656 | 0.784 |
| AA | 9.30 | 11.59 | 7.90 | 6.45 |
| L* | 94.55 | 94.53 | 91.98 | 93.60 |
| a* | −0.14 | −0.14 | 0.10 | 0.00 |
| b* | 1.25 | 1.28 | 2.66 | 1.96 |
| % Haze | 1.39 | 1.48 | 8.10 | 6.01 |
| Stress-crack time (hrs) | 1.19 | 1.01 | 0.93 | 2.05 |
| COF (lb-f) | 1.76 | 2.06 | 1.08 | 1.69 |
| O2 BIF (bottle sidewall) | 1.00 | 1.00 | 1.530 | 1.470 |

It can be readily seen that the bottles made from resin from Example 16 exhibited equivalent stress crack performance to the control even though the IV was over 0.11 dl/g lower, and the bottles made from resin from Example 17 exhibited double the stress-crack performance as the control at the same IV. It can also be seen that the bottle COF was lower for bottles made from both the Example 16 and Example 17 resins. Most importantly, the oxygen BIF was ~1.5 for bottle sidewalls made from both Example 16 and Example 17 resins, even though the amount of metal phosphonate present in each was only 500 ppm.

Example 19

Zinc(octylphosphonate) from Example 14 was melt blended into 0.84 dl/g IV PET at a 1000 ppm loading in a twin screw extruder. The resulting amorphous polymer was identical in appearance with respect to color and haze when compared to a PET control processed under the same conditions. The polymer was then crystallized and solid-state polymerized to rebuild the IV to 0.82 dl/g. It was observed that the PET containing zinc(octylphosphonate) exhibited about a 21% slower rate of IV increase to that observed for at PET control under identical conditions. Modeling of the solid-state polymerization reaction showed that this decrease in rate of IV build was consistent with a barrier improvement factor (BIF) of about 2.0.

Example 20

Calcium bis(octylphosphonate) from Example 15 was melt blended into 0.84 dl/g IV PET at a 1000 ppm loading in a twin screw extruder. The resulting amorphous polymer was identical in appearance with respect to color and haze when compared to a PET control processed under the same conditions. The polymer was then crystallized and solid-state polymerized to rebuild the IV to 0.82 dl/g. The PET containing calcium bis(octylphosphonate) exhibited a rate of IV increase 56% slower than that observed for at PET control under identical conditions. Modeling of the solid-state polymerization reaction showed that this decrease in rate of IV build was consistent with a barrier improvement factor (BIF) of about 4.5.

Example 21

PET polymer from Example 19 (containing 1000 ppm of zinc octylphosphonate) was injection molded into 24 gram preforms. At the same time, a control (PET that had been twin screw compounded, then solid-state polymerized to 0.82 dl/g IV) was injection molded into 24 gram preforms. Both sets of preforms were blow molded under identical conditions into 20 oz. generic bottles. 25 bottles from each variable were subjected to an accelerated stress-crack test wherein the bottles were pressurized to 4.0 volumes with $CO_2$ and the bottle bases submerged in a 0.2% caustic solution for 4.0 hours. The average time to failure for the control was 2.42 hours +/−0.46 hours, with all the control bottles failing within 190 minutes. In contrast, after 4.0 hours, none of the 25 bottles containing 1000 ppm of zinc octylphosphonate had failed. The IV of the control bottles was 0.788 dl/g; the IV of the test bottles was essentially the same at 0.796 dl/g.

The foregoing description includes the best mode for practicing the invention as understood by the inventor at the time of filing the application for letters patent. While the best mode has been described in the context of exemplary embodiments, the invention is not limited to the best mode or any of the exemplary embodiments.

I claim:

1. A composition comprising a polymer and at least one exfoliated layered metal phosphonate wherein said metal phosphonate comprises at least one divalent metal or trivalent metal.

2. presented) The composition of claim 1, wherein the polymer is a polyester, a polyamide, a polyolefin, a polyvinyl, a polyether, a polycarbonate, and mixtures thereof.

3. The composition of claim 1, wherein said exfoliated layered metal phosphonate comprises a divalent metal selected from the group consisting of magnesium, calcium, zinc, cobalt, nickel, and mixtures thereof.

4. The composition of claim 1, wherein the metal phosphonate comprises a first phosphonate R-group having a first length, and a second phosphonate R-group having a second length that is different than the first length.

5. The composition of claim 4, wherein the polymer comprises poly(ethylene terephthalate).

6. The composition of claim 4, wherein the first R-group comprises hydrogen, hydroxyl, or a hydrocarbon comprising between 1 to 12 carbon atoms, inclusively.

7. The composition of claim 4, wherein the second R-group comprises a hydrocarbon comprising between 1 to 16 carbon atoms, inclusively.

8. The composition of claim 1, wherein the polymer comprises poly(ethylene terephthalate).

9. An article formed of the composition of claim 1.

10. A container formed of the composition of claim 1.

11. A beverage container formed of the composition of claim 1.

12. A process for making polymer compositions, comprising:
providing a polymer;
providing at least one layered metal phosphonate;
incorporating the metal phosphonate into the polymer to form a metal phosphonate/polymer mixture; and
mixing the metal phosphonate/polymer mixture to achieve exfoliation of the metal phosphonate.

13. The process of claim 12, wherein the at least one layered metal phosphonate comprises a first phosphonate R-group having a first length, and a second phosphonate R-group having a second length that is different than the first length.

14. The process of claim 13, wherein the polymer comprises poly(ethylene terephthalate).

15. The process of claim 14, wherein the first R-group comprises hydrogen, hydroxyl, or a hydrocarbon comprising between 1 to 12 carbon atoms, inclusively.

16. The process of claim 14, wherein the second R-group comprises a hydrocarbon comprising between 1 to 16 carbons atoms, inclusively.

17. The process of claim 12, wherein the polymer comprises poly(ethylene terephthalate).

18. A process for making an article, comprising:
providing a composition comprising a polymer and at least one exfoliated layered metal phosphonate; and
forming the polymer composition using injection molding into a configuration that provides said article.

19. The process of claim 18, wherein said polymer composition formed using injection molding comprises polyethylene terephthalate.

20. The process of claim 18, wherein said container is a beverage container.

21. An article comprising more than one layer, wherein at least one layer comprises a composition according to claim 1.

22. The composition of claim 1 wherein said exfoliated layered metal phosphonate is a trivalent metal selected from the group consisting of lanthanum, aluminum, iron, and mixtures thereof.

23. The composition of claim 1 wherein said metal phosphonate comprises at least one functionalized R-group.

24. The composition of claim 23 wherein said at least one R-group comprises a functional group selected from hydroxyl, carboxyl, amino, amido, thio, vinyl, ether, ester, halo, and mixture thereof.

25. The composition of 23 wherein said at least one functionalized R-group increases the affinity of said metal phosphonate for the polymer.

26. The composition of claim 1, wherein the polymer comprises a polyolefin.

27. The composition of claim 26, wherein the polyolefin comprises a polyethylene, polypropylene, or blend or copolymer thereof.

28. The composition of claim 1 wherein said at least one exfoliated layered metal phosphonate is formed by incorporating an exfoliatable metal phosphonate into the polymer before or during polymerization.

29. The composition of claim 1 wherein said at least one exfoliated layered metal phosphonate and said polymer in combination are operative to provide enhanced barrier properties when compared to polymer not combined with said at least one exfoliated layered metal phosphonate.

30. The process of claim 12 wherein the metal phosphonate comprises at least one functionalized R-group.

31. The process of claim 12 wherein the mixing occurs while the polymer is in a molten state.

32. A process for making an article, comprising:
providing a composition comprising a molten polymer and at least one exfoliated layered metal phosphonate; and
forming the polymer composition into a solid configuration that provides said article.

33. The process of claim 32 wherein the step of forming comprises an injection molding technique.

34. The process of claim 33 wherein said container is a beverage container.

35. A container formed from a composition comprising a polymer and at least one exfoliated metal phosphonate, wherein the at least one metal phosphonate comprises at least one functionalized R-group.

36. The container of claim 35 wherein the metal phosphonate comprises at least one functionalized R-group selected from hydroxyl, carboxyl, amine, amido, thio, vinyl, ether, ester, halo, and mixtures thereof.

37. The container of claim 35 wherein said at least one functionalized R-group is operative to increase the affinity of the metal phosphonate for the polymer.

38. A container formed from a composition comprising a polymer and at least one exfoliated metal phosphonate, wherein the metal phosphonate comprises a first phosphonate R-group having a first length, and a second phosphonate R-group having a second length that is different from said first length.

39. The container of claim 38 wherein the polymer is poly(ethylene terephthalate).

40. The container of claim 38 wherein the first R-group is selected from the group consisting of hydrogen, hydroxyl, and a hydrocarbon having from 1 to not more than 12 carbon atoms.

41. The container of claim 38 wherein the second R-group is a hydrocarbon having from 1 to not more than 16 carbon atoms.

42. A container formed from a composition comprising a polymer and at least one exfoliated metal phosphonate having a lateral dimension greater than 0.25 microns.

43. A beverage container formed from a composition comprising a polymer and at least one exfoliated metal phosphonate having a lateral dimension greater than 0.25 microns.

44. A process for making a polymer composition, comprising:
providing at least one polymer precursor;
providing at least one layered metal phosphonate;
combining said at least one polymer precursor and at least one layered metal phosphonate to form a metal phosphonate/polymer precursor mixture; and
melt processing said mixture to effectuate exfoliation of said at least one layered metal phosphonate within said mixture.

45. The process of claim 44 wherein said melt processing comprises polymerization of said at least one polymer precursor.

46. The process of claim 44 wherein said metal phosphonate is placed in a liquid before said metal phosphonate is incorporated into said polymer.

47. The process of claim 46 wherein said metal phosphonate is placed in a liquid and subjected to heat, ultrasound, mixing, or milling to increase the rate or degree of exfoliation in the solvent, prior to said metal phosphonate being incorporated into said polymer.

48. A process for making an article, comprising:
providing a composition comprising a polymer and at least one exfoliated layered metal phosphonate; and
forming the polymer composition, using a melt process, into a configuration that provides said article.

49. The process of claim 48 wherein said polymer composition formed using said melt process comprises polyethylene terephthalate.

50. The process of claim 48 wherein said container is a beverage container.

51. A beverage container, comprising:
a polymer composition having a polymer selected from the group consisting of polyester, polyamide, polyolefin, polyvinyl, polyether, and polycarbonate;
at least one exfoliated layered metal phosphonate composition comprising at least one divalent metal or trivalent metal; and
said polymer composition and said metal phosphonate composition having been formed, using a melt process, into a configuration providing said beverage container.

52. A container formed from a composition comprising a polymer and at least one exfoliated metal phosphonate.

53. A beverage container formed from a composition comprising a polymer and at least one exfoliated metal phosphonate.

* * * * *